(12) United States Patent
Carlson

(10) Patent No.: US 10,617,288 B2
(45) Date of Patent: Apr. 14, 2020

(54) USER ASSISTANCE SYSTEM COMPRISING A CLEANING AND DISINFECTING DEVICE

(71) Applicant: OLYMPUS WINTER & IBE GMBH, Hamburg (DE)

(72) Inventor: Torben Carlson, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 117 days.

(21) Appl. No.: 15/447,333

(22) Filed: Mar. 2, 2017

(65) Prior Publication Data
US 2017/0172398 A1 Jun. 22, 2017

Related U.S. Application Data

(63) Continuation of application No. PCT/EP2015/069123, filed on Aug. 20, 2015.

(30) Foreign Application Priority Data

Sep. 3, 2014 (DE) .......... 10 2014 217 559

(51) Int. Cl.
A61B 1/12 (2006.01)
A61B 90/96 (2016.01)
(Continued)

(52) U.S. Cl.
CPC .......... A61B 1/123 (2013.01); A61B 1/00048 (2013.01); A61B 1/00059 (2013.01);
(Continued)

(58) Field of Classification Search
USPC .......................................... 348/61
See application file for complete search history.

(56) References Cited

U.S. PATENT DOCUMENTS 7,726,564 B2 6/2010 Goldbach
2002/0161460 A1* 10/2002 Noguchi ............ A61B 1/00059
700/90
2013/0278631 A1* 10/2013 Border ................ G02B 27/017
345/633

FOREIGN PATENT DOCUMENTS

DE 19703822 A1 6/1998
EP 1952779 A1 8/2008
(Continued)

OTHER PUBLICATIONS

International Search Report dated Feb. 11, 2016 issued in PCT/EP2015/069123.
(Continued)

Primary Examiner — James M Anderson, II
(74) Attorney, Agent, or Firm — Scully, Scott, Murphy & Presser, P.C.

(57) ABSTRACT

A user assistance system for use with a device for cleaning and disinfecting a surgical instrument. The system including data eyeglasses including a camera and a projection surface, wherein the data eyeglasses projects information on the projection surface, a data storage in which a plurality of data sets on different types of surgical instruments are saved, information relating to an identifying feature of a particular type of surgical instrument and visual data relating to instructions on cleaning the particular type or surgical instrument are in each data set, and a controller configured to capture an image of a surgical instrument to be cleaned, compare image data with the identifying feature in the data sets, identify a type of the surgical instrument to be cleaned using the identifying feature in the image, and display visual information relating to instructions on cleaning the identified type of surgical instrument on the projection surface.

17 Claims, 1 Drawing Sheet

(51) Int. Cl.
  *A61B 90/00*   (2016.01)
  *A61B 90/70*   (2016.01)
  *A61B 90/98*   (2016.01)
  *A61B 1/00*    (2006.01)
  *G02B 27/01*   (2006.01)
  *G06K 9/62*    (2006.01)
  *A61B 90/50*   (2016.01)
  *A61B 34/00*   (2016.01)
  *G06K 9/46*    (2006.01)

(52) U.S. Cl.
  CPC ............ *A61B 90/361* (2016.02); *A61B 90/70* (2016.02); *A61B 90/96* (2016.02); *A61B 90/98* (2016.02); *G02B 27/0172* (2013.01); *G06K 9/6201* (2013.01); *G06K 9/6267* (2013.01); *A61B 2034/256* (2016.02); *A61B 2090/502* (2016.02); *A61B 2090/701* (2016.02); *G02B 2027/014* (2013.01); *G02B 2027/0138* (2013.01); *G02B 2027/0141* (2013.01); *G02B 2027/0178* (2013.01); *G06K 9/46* (2013.01); *G06K 2209/05* (2013.01)

(56) References Cited

FOREIGN PATENT DOCUMENTS

| JP | 2009-291308 A | 12/2009 | |
| JP | 2009291308 A * | 12/2009 | ............. A61B 90/70 |
| JP | 2013-106790 A | 6/2013 | |
| WO | WO-2015175681 A1 * | 11/2015 | |

OTHER PUBLICATIONS

Google Glass, Wikipedia, URL:http://de.wikipedia.org/wiki/Google_Glass, published on Aug. 19, 2014, retrieved from Wayback Machine, with English translation.

* cited by examiner

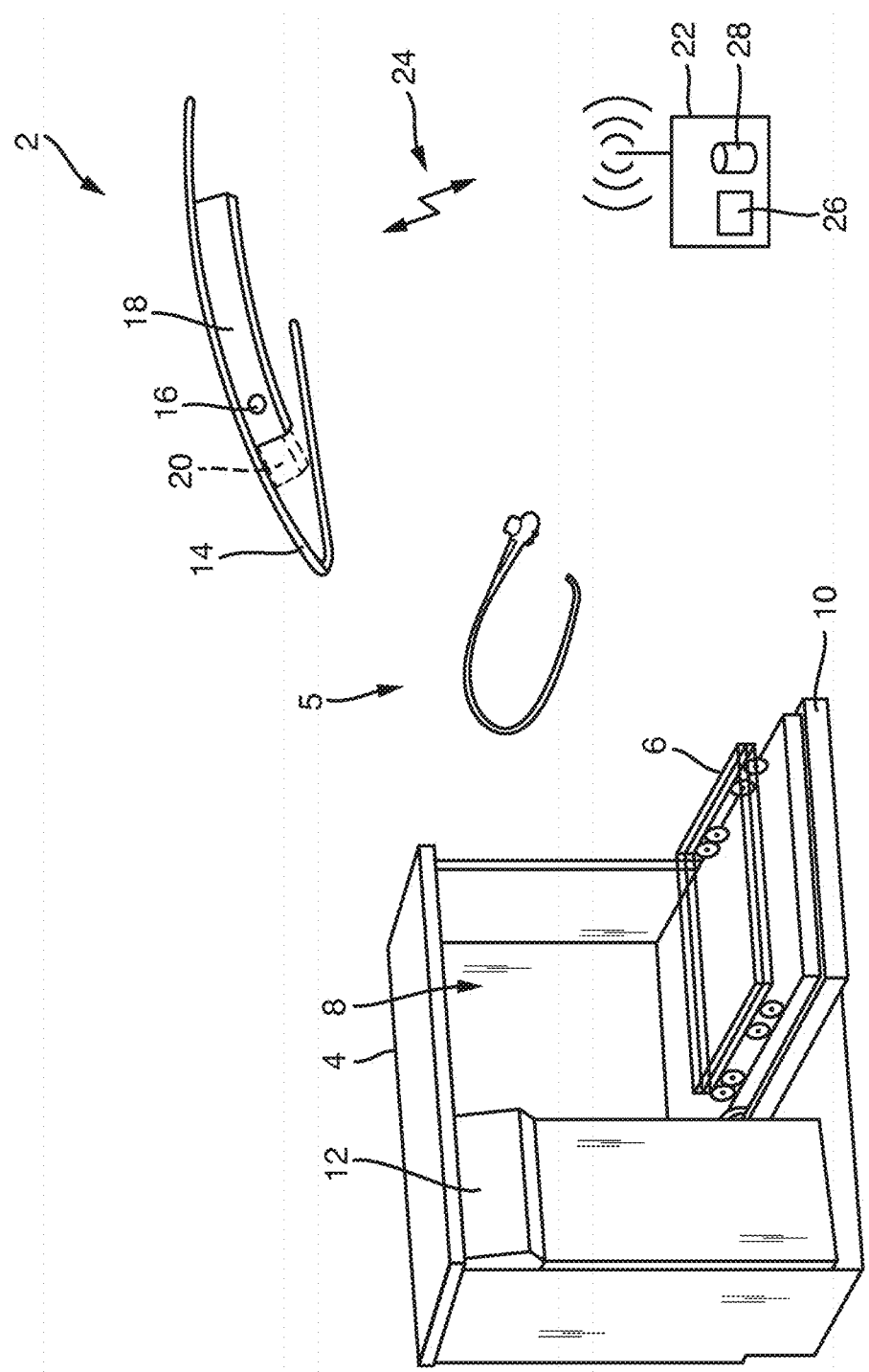

USER ASSISTANCE SYSTEM COMPRISING A CLEANING AND DISINFECTING DEVICE

CROSS-REFERENCE TO RELATED APPLICATION

The present application is a continuation of PCT/EP2015/069123 filed on Aug. 20, 2015, which is based upon and claims the benefit to DE 10 2014 217 559.3 filed on Sep. 3, 2014, the entire contents of each of which are incorporated herein by reference.

BACKGROUND

Field

The present application relates to a user assistance system of a cleaning and disinfecting device for cleaning and disinfecting surgical instruments. Moreover, the present application relates to a method for operating such a user assistance system. The present application also relates to a cleaning and disinfecting device comprising a user assistance system as well as a computer program product.

Prior Art

Stringent requirements are placed on the reprocessing, i.e., cleaning and disinfecting of surgical instruments. For reprocessing to be successful, surgical instruments, such as an endoscope, must be inserted into the cleaning and disinfection device in accordance with the manufacturer's instructions and, if necessary, connected to the device's connections.

The variety of surgical instruments used in a clinical environment requires a great deal of expertise on the part of the individuals charged with reprocessing. For example, endoscopes of different types must be placed differently in the cleaning basket of the cleaning and disinfection device and connected to different connections. To assist the individuals tasked with cleaning, the various connections and insertion positions are described in detail in the user manual of the cleaning and disinfecting device. In addition, brief instructions in the form of laminated flyers are widespread. Simultaneously handling a surgical instrument and a leaflet is, however, cumbersome. Moreover, the up-to-dateness or availability of such brief instructions is not ensured.

SUMMARY

An object is to present a user assistance system of a cleaning and disinfection device, a cleaning and disinfection device, a method for operating a user assistance system, as well as a computer program product, wherein the operation of the cleaning and disinfecting device is simplified.

Such object can be solved by a user assistance system of a cleaning and disinfection device for cleaning and disinfecting surgical instruments, wherein the user assistance system is further developed in that the user assistance system comprises data eyeglasses which have a camera and an imaging optical module with a projection surface, wherein the imaging optical module is configured to project information on a projection surface arranged in the field of vision of the user of the data eyeglasses, and wherein a data storage is also provided in which a plurality of data sets on different types of surgical instruments are saved, wherein information relating to an identifying feature of a particular type of surgical instrument and visual data relating to instructions on cleaning this type are in each data set, and wherein the user assistance system is furthermore configured to capture with the camera an image of a surgical instrument to be cleaned, to compare the image data of the image with the identifying features in the data sets, to identify a type of the surgical instrument to be cleaned using an identifying feature in the image, and to display visual information relating to instructions on cleaning this type on the projection surface by means of the optical module.

Thus, the individual tasked with cleaning and disinfecting, such as a hospital employee, has both hands free when preparing the surgical instrument for reprocessing to correctly and reliably insert, or respectively connect, the surgical instrument. The need to simultaneously consult a flier or manual during this activity can be eliminated. The hospital employee has the surgical instrument to be cleaned in his field of vision and, at the same time, information on how to handle it.

The information to be provided can be, for example, an explanatory text, and/or a picture or a sketch that explains the manipulations to perform. Handling instructions in the sense of augmented reality can also be provided. A machine-side connection to be used and an instrument-side plug can be highlighted. For example, the relevant areas can be highlighted in color or marked with an illuminated frame. It is also provided for the correct position of the surgical instrument to overlap the image visible to the user. A virtual instrument or its simplified or schematic representation are for example merged with the real image, or respectively superimposed thereupon.

The user assistance system simplifies and accelerates the reprocessing of surgical instruments. At the same time, the user is guided and supported in handling and use so that the reprocessing procedure is less error-prone.

The data set relating to the cleaning of different types of surgical instruments can be saved in an electronic database. This data can be updated quickly, easily and problem-free by updating one or more files saved in the data storage. In terms of speed and cost, this method is clearly superior to interchanging numerous fliers.

The user assistance system can further comprise a plurality of additional data sets for different types of holding apparatuses, such as cleaning baskets of cleaning and disinfecting devices, that can be saved in the data storage, wherein information relating to an identifying feature of a particular type of holding apparatus and visual information relating to the cleaning of surgical instruments using this type are in each of these data sets, wherein the user assistance system can be furthermore configured to additionally capture an image of a holding apparatus with the camera, to compare the image data of the image with the identifying features in the additional data sets, to identify a type of the holding apparatus using an identifying feature in the image, and to display visual information relating to the cleaning of the surgical instrument using this type of holding apparatus on the projection surface by means of the optical module.

Different types of holding apparatuses, such as those used for example in different series or types of cleaning and disinfecting devices, necessitate that the surgical instruments to be cleaned are handled differently. For example, the connections to which the surgical instrument is to be connected for reprocessing are at different positions. Furthermore, the surgical instrument is often inserted differently in different types of holding apparatuses.

Not only the type of surgical instrument, but also the type of holding apparatus can be recognized by a user assistance system according to the cited embodiment. Information is provided that relates to the handling of the recognized type of surgical instrument when the recognized type of holding apparatus is used. All necessary information is available to the hospital employee to correctly place the surgical instrument to be cleaned into the holding apparatus. Effective cleaning and disinfection is ensured.

According to one embodiment, the user assistance system can further comprise the identifying feature being at least part of an external appearance and/or shape of the surgical instrument or the holding apparatus, and/or the identifying feature is at least part of a machine-readable code in or on the surgical instrument or holding apparatus.

The machine-readable code can be a barcode and/or a QR code. The data eyeglasses can be configured to independently identify the type of surgical instrument and/or the holding apparatus using the captured image data of one or more of the cited identifying features. Additional handling on the part of user is unnecessary. The user is enabled to concentrate on his actual tasks, i.e., correctly handling the surgical instrument.

In terms of its user-friendliness, the user assistance system according to the invention is superior to other electronic user assistance systems. The necessity of using an input unit, such as a touchpad or keyboard, can be eliminated. The use of a scanner, such as for capturing a barcode, can be eliminated. With the cited solutions, the danger always exists of these units coming into contact with the contaminated surgical instrument, which is undesirable. By using data eyeglasses in the user assistance system, this can be avoided.

According to a development of the user assistance system, the visual information relates to the insertion of the surgical instrument into the holding apparatus, and/or the connection of the surgical instrument to connections of the holding apparatus.

This embodiment can be used for endoscopes as surgical instruments. They make it easier for the individual tasked with cleaning and disinfecting to reprocess the endoscope. Endoscopes possess a plurality of connections that must be connected to various hoses or couplings of the cleaning and disinfecting device before cleaning and disinfecting. Given the variety of endoscopes in a hospital environment, hospital personnel routinely experience problems with correctly assigning the connections. With the user assistance system according to the cited embodiment, the hospital employee can be provided with all the necessary information, so that correctly connecting the endoscope is simplified.

According to another embodiment, the user assistance system can further comprise the data eyeglasses further comprising an audio output apparatus, and audio data comprising instructions on cleaning the surgical instrument that supplement the visual data are in at least one data set, and/or in at least one additional data set.

The cited audio files can comprise instructions on handling and cleaning the surgical instrument and support the visual depiction. The audio instructions can be output synchronized with the visual depictions relating to the handling of the surgical instrument. Accordingly, the provided visual data and, for example, spoken handling instructions can compliment each other. The handling of the surgical instrument to reprocess it is further simplified.

In another embodiment, the projection surface can be part of a transparent prism, wherein along the line of sight, a user of the data eyeglasses can observe both the field of vision as well as information projected on the projection surface through the part of the prism comprising the projection surface.

Glass or a transparent plastic, such as Plexiglas®, can be provided as the material for the prism. Such a system should not block the field of vision of the user. The user looks unrestrictedly through the prism and keeps track of the objects in his own field of vision while he is provided with the information necessary for reprocessing the surgical instruments.

According to another embodiment, the data eyeglasses can comprise data storage. The data storage can be a non-volatile data storage. According to an alternative embodiment, the data storage can be outside of the data eyeglasses, and the data eyeglasses can comprise a transmitting/receiving unit for establishing a wired or wireless data link with the data storage.

The data storage can be in a central data processing unit (server). The data storage can be a central data storage that can be accessed by a plurality of data eyeglasses, possibly from different user assistance systems. The data eyeglasses can be furthermore assigned to different cleaning and disinfecting devices. An advantage of a central administration of the information relating to the handling of different surgical instruments and/or different holding apparatuses can be that the updating of the data can be carried out with very little effort.

The user assistance system can further comprise the surgical instrument being an endoscope. Endoscopes are available as surgical instruments in a plurality of different types for different uses and some of them must be handled very differently from others. To correctly reprocess endoscopes, a plurality of individual steps can be performed, and a wide range of details can be observed with regard to their handling. This necessitates having and following a user manual for each endoscope. The reprocessing of endoscopes can be greatly simplified and more reliable and safer when the information relevant to reprocessing is compiled in a database and conveniently provided to the user.

The data eyeglasses of the user assistance system offer their user the functionality of a heads-up display. The data eyeglasses can be optionally monocular or binocular data eyeglasses. In other words, the provided information is shown in the field of vision of one or both eyes of the user. In terms of their functionality, the data eyeglasses are a small computer that can be worn on the head. They can comprise a central processing unit (CPU), working memory (RAM), a microphone, a digital camera directed in the line of sight, a speaker such as a bone conduction speaker, an antenna for receiving signals via a wireless data transmission path, such as an antenna for receiving signals via Bluetooth, WLAN, UMTS, 3G, etc., an acceleration sensor and an energy store (rechargeable battery).

The central processor, such as a microprocessor, can be configured to process the captured image data and control the imaging optical module. If the data storage is located in the data eyeglasses, the central processor can be configured to identify at least one identifying feature in the captured image data, retrieve data sets from the data storage, and compare the identifying features available therein. The central processor can then retrieve the visual data and/or the audio data from the associated data set and provide them to the imaging optical module, and/or the audio output unit.

If the data storage is located in a central server, the central processor of the data eyeglasses can be configured to optionally transmit the captured image data to the server, or to request and receive data sets therefrom. An analysis of the captured image data can alternatively occur in the central processor of the data eyeglasses or on the server. Depending on whether the analysis is performed decentralized or centralized, a comparison of the identifying feature with the saved identifying features occurs decentralized or centralized. Then the visual data and/or the audio data can be retrieved from the associated data set, transmitted to the data eyeglasses, and provided to the imaging optical module and/or the audio output unit.

The aforementioned aspects can be applicable to all embodiments.

Such object can be furthermore solved by a cleaning and disinfecting device comprising a user assistance system according to one or more of the cited embodiments. The same or similar features as already explained with reference to the user assistance system can apply to the cleaning and disinfecting device.

Such object can be also solved by a method for operating a user assistance system according to one or more of the cited embodiments, wherein the method comprises:

capturing, with a camera, an image of a surgical instrument to be cleaned, comparing the image data of the image with identifying features in the data sets, identifying a type of surgical instrument to be cleaned using an identifying feature in the image and, by means of the optical module, displaying on the projection surface visual information relating to instructions for cleaning the identified type.

The same or similar features as already explained with reference to the user assistance system can apply to the method for operating the user assistance system.

According to one embodiment, the method can further comprise a plurality of additional data sets for different types of holding apparatuses, such as cleaning baskets of cleaning and disinfecting devices, can be saved in the data storage, wherein information relating to an identifying feature of a particular type of holding apparatus and visual information relating to the cleaning of surgical instruments using this type are in each of these data sets, wherein the method furthermore comprises:

capturing an additional image of a holding apparatus with the camera, comparing the additional image with the identifying features in the data sets, identifying a type of holding apparatus using an identifying feature in the additional image, and by means of the optical module, displaying on the projection surface visual information relating to the cleaning of the surgical instrument using the identified type of holding apparatus.

According to an additional embodiment of the method for operating a user assistance system, the identifying feature can be at least part of an external appearance and/or shape of the surgical instrument, and/or cam be at least part of a machine-readable code in or on the surgical instrument or holding apparatus.

The method for operating a user assistance system can further comprise the data eyeglasses further comprising an audio output apparatus, and instructions on cleaning the surgical instrument comprising audio data that supplement the visual data are in at least one data set, and/or at least one additional data set, and audio data supplementing visual information are output.

The same or similar features as already explained with reference to the analogous embodiments of the user assistance system also apply to the cited embodiments of the method.

Such object can also be solved by a computer program product that causes data eyeglasses and a user assistance system according to one or more of the cited embodiments to execute a method according to one or more of the cited embodiments.

BRIEF DESCRIPTION OF THE DRAWINGS

Further features will become apparent from the description of embodiments a together with the claims and the included FIGURE. Embodiments can fulfill individual features or a combination of several features.

The embodiments will be described below without restricting the general inventive idea with reference to the FIGURE, and for any details which are not explained further in the text, express reference is made to the FIGURE.

The FIGURE illustrates a schematic user assistance system of a cleaning and disinfecting device with data eyeglasses.

In the FIGURE, same or similar elements and/or parts are provided with the same reference numbers in order to prevent the item from needing to be reintroduced.

DETAILED DESCRIPTION

The FIGURE shows a user assistance system 2 for use with a cleaning and disinfecting device 4. The cleaning and disinfecting device 4 serves to reprocess, i.e., clean and disinfect, surgical instruments 5, such as, endoscopes.

Before the surgical instruments 5 are reprocessed, they are inserted into a holding apparatus 6 such as a cleaning basket. Moreover, the surgical instruments 5, especially when they are endoscopes, are connected to connections (not shown in the FIGURE) of the cleaning and disinfecting device 4. This is followed by the reprocessing of the surgical instruments 5 in a rinsing chamber 8 that is sealed by the door 10. The parameters for cleaning and disinfecting the surgical instruments 5 are, if necessary, entered using a control panel 12 on the front of the cleaning and disinfecting device 4.

The user assistance system 2 comprises data eyeglasses 14. Monocular data eyeglasses 14 are depicted as an example. Binocular data eyeglasses 14 can also be used. The data eyeglasses 14 comprise a camera 16 with an imaging direction pointing in the line of sight of a user of the data eyeglasses 14. Furthermore, the data eyeglasses 14 comprise an imaging optical module that is arranged within a housing 18. The imaging optical module comprises an image-generating unit such as a microprojector, optical units such as a collimator and a prism 20 that comprises a projection surface. The projection surface is for example an exterior of the prism 20. The prism 20 is for example made of glass or Plexiglas® so that a user of the data eyeglasses can look unrestrictedly through the prism 20.

An individual involved in cleaning the surgical instrument 5 uses the user assistance system 2 by first putting on the data eyeglasses 14 and looking at the surgical instrument 5. An image of the surgical instrument 5 is captured with the assistance of the camera 16. The image data of this image is analyzed for an identifying feature of the surgical instrument 5. The identifying feature is in particular at least part of an external appearance and/or shape of the surgical instrument 5. Furthermore, the identifying feature can be at least part of a machine-readable code such as a barcode or a QR code.

In the exemplary embodiment depicted in the FIGURE, the analysis of the image occurs in a server 22 that is in contact with the data eyeglasses 14 via a wireless data link 24. For this purpose, the data eyeglasses 14 are equipped with a transmitting/receiving unit. The same holds true for the server 22. The image data captured with the camera 16 are transmitted by the wireless data link 24 to the server 22 and processed there in a central processor 26.

The server 22 can further comprises a data storage 28 in which a plurality of data sets for various types of surgical instruments 5 are saved. Each of these data sets comprises information relating to an identifying feature of a specific type of surgical instrument 5. For example, information relating to an external appearance and/or a shape of different types of surgical instruments 5 are in such a data set. It is furthermore possible to provide surgical instruments 5 of an identical type with an equivalent machine-readable code so that they can be identified in this manner as surgical instruments 5 of the same type.

Instructions on cleaning surgical instruments 5 of different types are also in the data sets in the data storage 28. In particular, this information is visual data. Images, sketches, moving animations or film sequences are suitable that display the handling of the identified type in preparation for cleaning and disinfecting. It is for example explained how the identified type of endoscope can be inserted into the holding apparatus 6 of the cleaning and disinfection device 4, and how certain connections of the endoscope are to be connected to certain connections of the cleaning and disinfecting device 4.

The image data are transmitted via the wireless data link 24 from the server 22 to the data eyeglasses 14. With the assistance of the optical module, the data eyeglasses depict the image data on the projection surface of the prism 20.

The user of the user assistance system 2 that wears the data eyeglasses 14 has the surgical instrument 5, the holding apparatus 6 as well as the information additionally provided by the eyeglasses in his field of vision. At the same time, both hands are free so that the surgical instrument 5 can be quickly and safely inserted and connected in the cleaning and disinfecting device 4.

According to another exemplary embodiment, a plurality of additional data sets are in the data storage 28. These additional data sets relate to different types of holding apparatuses 6. For example, the data sets comprise information relating to the handling of different cleaning baskets of different cleaning and disinfecting devices 4. With the assistance of the data eyeglasses 14, or more precisely their camera 16, an identifying feature of the holding apparatus 6 is captured. Similar to the surgical instrument 5, this identifying feature is for example at least a part of the external appearance and/or shape of the holding apparatus 6. Furthermore, the holding apparatus 6 can be provided with a machine-readable code that at least partially serves as the identifying feature.

Image data of an image of the holding apparatus 6 are transmitted by the data eyeglasses 14 via the wireless data link 24 to the server 22. There, the central processor 26 performs a comparison with identifying features in the additional data sets and determines a type of the holding apparatus 6. Then, visual information relating to the cleaning of the surgical instrument 5 using this special type of holding apparatus 6 is transmitted via the wireless data link 24 to the data eyeglasses 14. Using the optical module, the data eyeglasses depict the information on the projection surface.

The information relating to the handling of the holding apparatus 6 can be combined with the information relating to the handling of the surgical instrument 5. In other words, the user receives specific instructions on how to handle the recognized type of surgical instrument 5 using the recognized holding apparatus 6. For example, the user is shown how to insert a special type of endoscope in a specific cleaning basket of a cleaning and disinfecting device 4, and which connections of the endoscope are to be connected to which connecting hoses or connectors of the cleaning and disinfecting device 4.

The visual data can be supported by audio data, such as spoken instructions. For this purpose, these supplementary audio data are in the data storage 28 in addition to the visual data. The supplementary audio data are transmitted together with the data relating to the visual instructions via the wireless data link 24. For example, audio comments or instructions are provided to the user together with explanatory sketches. To play back the audio data, the data eyeglasses 14 have an audio output apparatus such as a speaker or bone conduction speaker.

According to another exemplary embodiment, the data storage 28 and central processor 26 can be located within the housing 18 of the data eyeglasses 14. The captured image data are evaluated and compared with data sets in the data storage 28 within the data eyeglasses 14.

Furthermore, the server 22 can be connected to a plurality of data eyeglasses 14. Advantageously, the data storage 28 is available to a plurality of data eyeglasses 14 so that by updating the data on this central data storage 28, all of the data eyeglasses 14 have access to current data sets.

According to an alternative exemplary embodiment, the data in the data storage 28 are updated when the data storage is provided in a decentralized manner as part of the data eyeglasses 14 via the wireless data link originating from the server 22.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE NUMBER LIST

2 User assistance system
4 Cleaning and disinfecting device
5 Surgical instrument
6 Holding apparatus
8 Rinsing chamber
10 Door
12 Control panel
14 Data eyeglasses
16 Camera
18 Housing
20 Prism
22 Server
24 Wireless data connection
26 Central processor
28 Data storage

What is claimed is:

1. A user assistance system for use with a cleaning and disinfection device for cleaning and disinfecting a surgical instrument, the user assistance system comprising:
  data eyeglasses comprising:
  a camera; and
  a projection surface, wherein the data eyeglasses is configured to project information on the projection surface arranged in a field of vision of a user of the data eyeglasses,
  a data storage in which a plurality of data sets on different types of surgical instruments are saved, wherein information relating to an identifying feature of a particular type of surgical instrument and visual information relating to instructions on how to clean the particular type of surgical instrument are in each data set, wherein the data storage further comprises a plurality of additional data sets for different types of holding apparatuses of the cleaning and disinfection device, wherein information relating to an identifying feature of a particular type of holding apparatus and visual information relating to the cleaning of the different types of surgical instruments using the particular type of holding apparatus are in each of the additional data sets, and a controller configured to:
  capture, with the camera, an image of a surgical instrument to be cleaned,
  capture an additional image of a holding apparatus to be used with the camera,
  compare image data corresponding to the image with the identifying feature in the data sets,
  compare image data corresponding to the additional image with the identifying feature in the additional data sets,
  identify a type of the surgical instrument to be cleaned using the identifying feature in the image,
  identify a type of the holding apparatus to be used using the identifying feature in the image,
  display the visual information relating to instructions on how to clean the identified type of surgical instrument on the projection surface; and
  display the visual information relating to how to clean the surgical instrument using the identified type of holding apparatus on the projection surface.

2. The user assistance system according to claim 1, wherein the identifying feature is one or more of at least part of an external appearance of the surgical instrument, at least part of an external shape of the surgical instrument and at least part of a machine-readable code in or on the surgical instrument.

3. The user assistance system according to claim 1, wherein the identifying feature is one or more of at least part of an external appearance of the holding apparatus, at least part of an external shape of the holding apparatus and at least part of a machine-readable code in or on the holding apparatus.

4. The user assistance system according to claim 1, wherein the visual information relates to one or more of the insertion of the surgical instrument into the holding apparatus and the connection of the surgical instrument to connections of the holding apparatus.

5. The user assistance system according to claim 1, further comprising an audio output apparatus, and at least one data set of the plurality of data sets further includes audio data comprising instructions on how to clean the surgical instrument that supplement the visual data.

6. The user assistance system according to claim 1, further comprising an audio output apparatus, and at least one additional data set of the plurality of additional data sets further includes audio data comprising instructions on how to clean the surgical instrument that supplement the visual data.

7. The user assistance system according to claim 1, wherein the projection surface is part of a prism, wherein along a line of sight, the user of the data eyeglasses can observe both a field of vision as well as the visual information projected on the projection surface through the part of the prism comprising the projection surface.

8. The user assistance system according to one of claim 1, wherein the data eyeglasses comprise the data storage.

9. The user assistance system according to claim 1, wherein the data storage is outside of the data eyeglasses, and the data eyeglasses further comprise a transmitting/receiving unit for establishing one of a wired or wireless data link with the data storage.

10. The user assistance system according to claim 1, wherein the surgical instrument is an endoscope.

11. A cleaning and disinfecting device comprising the user assistance system according to claim 1.

12. A method for operating the user assistance system according to claim 1, wherein the method comprises:
  capturing, with the camera, the image of the surgical instrument to be cleaned,
  capturing an additional image of a holding apparatus to be used with the camera,
  comparing the image data of the image with the identifying feature in the data sets,
  comparing the additional image with the identifying feature in the data sets,
  identifying a type of surgical instrument to be cleaned using the identifying feature in the image,
  identifying a type of holding apparatus using an identifying feature in the additional image,
  displaying, on the projection surface, the visual information relating to the instructions; and
  displaying, on the projection surface, the visual information relating to how to clean the surgical instrument to be cleaned using the identified type of holding apparatus.

13. The method for operating a user assistance system according to claim 12, wherein the identifying feature is one or more of at least part of an external appearance of the surgical instrument, at least part of an external shape of the surgical instrument and at least part of a machine-readable code in or on the surgical instrument.

14. The method for operating a user assistance system according to claim 12, wherein the identifying feature is one or more of at least part of an external appearance of the holding apparatus, at least part of an external shape of the holding apparatus and at least part of a machine-readable code in or on the holding apparatus.

15. The method for operating a user assistance system according to claim 12, wherein the data eyeglasses further comprise an audio output apparatus, and at least one data set of the plurality of data sets further includes audio data comprising instructions on how to clean the surgical instrument that supplement the visual data, the method further comprising outputting the audio data to supplement the visual information.

16. The method for operating a user assistance system according to claim 12, wherein the data eyeglasses further comprise an audio output apparatus, and at least one additional data set of the plurality of additional data sets further includes audio data comprising instructions on how to clean the surgical instrument that supplement the visual data, the method further comprising outputting the audio data to supplement the visual information.

17. A computer-readable storage device storing instructions for operating a user assistance system for use with a cleaning and disinfection device for cleaning and disinfecting a surgical instrument, the user assistance system comprising data eyeglasses including a camera and a projection surface, wherein the data eyeglasses is configured to project information on the projection surface arranged in a field of vision of a user of the data eyeglasses, a data storage in which a plurality of data sets on different types of surgical instruments are saved, wherein information relating to an identifying feature of a particular type of surgical instrument and visual information relating to instructions on how to clean the particular type of surgical instrument are in each data set, wherein the data storage further comprises a plurality of additional data sets for different types of holding apparatuses of the cleaning and disinfection device, wherein information relating to an identifying feature of a particular type of holding apparatus and visual information relating to the cleaning of the different types of surgical instruments using the particular type of holding apparatus are in each of the additional data sets and a controller, the computer-readable storage device storing the instructions that, when executed, cause the controller to:

capture, with the camera, the image of the surgical instrument to be cleaned, capture an additional image of a holding apparatus to be used with the camera, compare the image data of the image with the identifying feature in the data sets, compare image data corresponding to the additional image with the identifying feature in the additional data sets, identify a type of surgical instrument to be cleaned using the identifying feature in the image, identify a type of the holding apparatus to be used using the identifying feature in the image, display, on the projection surface, the visual information relating to the instructions for how to clean the identified type of surgical instrument, and display the visual information relating to how to clean the surgical instrument using the identified type of holding apparatus on the projection surface.

* * * * *